US011633227B2

(12) United States Patent
Mensch et al.

(10) Patent No.: US 11,633,227 B2
(45) Date of Patent: *Apr. 25, 2023

(54) MEDICAL FORCEPS WITH OFFSET TEETH

(71) Applicant: GYRUS ACMI, INC., Southborough, MA (US)

(72) Inventors: John R. Mensch, Plymouth, MN (US); Zane R. Ward, Prior Lake, MN (US); Jeffrey J. Nelson, Maple Grove, MN (US); Huisun Wang, Maple Grove, MN (US); Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 355 days.

This patent is subject to a terminal disclaimer.

(21) Appl. No.: 16/413,835

(22) Filed: May 16, 2019

(65) Prior Publication Data

US 2019/0269455 A1 Sep. 5, 2019

Related U.S. Application Data

(63) Continuation of application No. 15/088,655, filed on Apr. 1, 2016, now Pat. No. 10,368,940.
(Continued)

(51) Int. Cl.
*A61B 18/14* (2006.01)
*A61B 17/29* (2006.01)
*A61B 18/12* (2006.01)

(52) U.S. Cl.
CPC ...... *A61B 18/1447* (2013.01); *A61B 18/1442* (2013.01); *A61B 2017/2926* (2013.01);
(Continued)

(58) Field of Classification Search
CPC .............. A61B 18/085; A61B 18/1442; A61B 18/1445; A61B 18/1447;
(Continued)

(56) References Cited

U.S. PATENT DOCUMENTS 2,397,823 A 4/1946 Walter
3,515,139 A 6/1970 Mallina
(Continued)

FOREIGN PATENT DOCUMENTS

CN 101912290 A 12/2010
CN 102421385 A 4/2012
(Continued)

OTHER PUBLICATIONS

Chinese First Office Action for Chinese Patent Application No. 201680020739.6; dated Jul. 25, 2019.
(Continued)

*Primary Examiner* — Thomas A Giuliani
(74) *Attorney, Agent, or Firm* — Schwegman Lundberg & Woessner, P.A.

(57) ABSTRACT

A forceps including a gripping assembly. The gripping assembly includes an upper jaw and a lower jaw. The upper jaw includes a proximal end and a distal end. The upper jaw includes an upper tooth having an upper proximally facing canted tooth surface and an upper distally facing canted tooth surface. The lower jaw includes a proximal end and a distal end. The lower jaw includes a socket having a lower distally facing canted socket surface and a lower proximally facing socket surface. The upper jaw, the lower jaw, or both are moveable so that the gripping assembly moves between an open position and a gripping position. In the gripping position, a gap is defined between the upper distally facing canted tooth surface and the lower proximally facing socket surface.

14 Claims, 7 Drawing Sheets

Related U.S. Application Data

(60) Provisional application No. 62/145,620, filed on Apr. 10, 2015.

(52) U.S. Cl.
CPC . *A61B 2017/2933* (2013.01); *A61B 2018/126* (2013.01); *A61B 2018/1455* (2013.01)

(58) Field of Classification Search
CPC .. A61B 2018/00607; A61B 2018/0063; A61B 2018/126; A61B 2018/1452; A61B 2018/1455; A61B 17/29; A61B 17/295; A61B 2017/2926; A61B 2017/2933
USPC ........ 606/41, 50–52, 207; 607/99, 101, 115, 607/116
See application file for complete search history.

(56) References Cited

U.S. PATENT DOCUMENTS

| | | | |
|---|---|---|---|
| 3,815,609 | A | 6/1974 | Chester |
| 4,784,136 | A | 11/1988 | Klein |
| 4,955,897 | A | 9/1990 | Ship |
| 5,059,214 | A | 10/1991 | Akopov et al. |
| 5,275,615 | A | 1/1994 | Rose |
| 5,304,203 | A | 4/1994 | El-Mallawany et al. |
| 5,458,598 | A * | 10/1995 | Feinberg ............ A61B 18/1445 606/205 |
| 5,573,535 | A | 11/1996 | Viklund |
| 5,590,570 | A | 1/1997 | LeMaire, III et al. |
| 5,667,526 | A | 9/1997 | Levin |
| 5,673,841 | A | 10/1997 | Schulze et al. |
| 5,752,973 | A | 5/1998 | Kieturakis |
| 5,769,849 | A | 6/1998 | Eggers |
| 5,819,738 | A | 10/1998 | Slater |
| 5,891,142 | A | 4/1999 | Eggers et al. |
| 5,964,779 | A | 10/1999 | Mayenberger et al. |
| 6,036,656 | A | 3/2000 | Slater |
| 6,162,220 | A | 12/2000 | Nezhat |
| 6,273,887 | B1 * | 8/2001 | Yamauchi .......... A61B 18/1445 606/51 |
| 6,736,813 | B2 * | 5/2004 | Yamauchi .......... A61B 18/1445 606/51 |
| 6,989,017 | B2 | 1/2006 | Howell et al. |
| 7,108,694 | B2 | 9/2006 | Miura et al. |
| 7,308,739 | B2 | 12/2007 | Andersen et al. |
| 7,749,222 | B2 | 7/2010 | Lu et al. |
| 7,887,535 | B2 | 2/2011 | Lands et al. |
| 7,996,963 | B2 | 8/2011 | Cameron |
| 8,262,655 | B2 | 9/2012 | Ghabrial et al. |
| 8,641,712 | B2 | 2/2014 | Couture |
| 8,647,343 | B2 | 2/2014 | Chojin et al. |
| 8,715,277 | B2 | 5/2014 | Weizman |
| 10,368,940 | B2 * | 8/2019 | Mensch ............ A61B 18/1447 |
| 2009/0326530 | A1 | 12/2009 | Orban, III et al. |
| 2010/0057058 | A1 | 3/2010 | Holcomb et al. |
| 2010/0057085 | A1 * | 3/2010 | Holcomb ........... A61B 18/1445 606/51 |
| 2010/0305564 | A1 | 12/2010 | Livneh |
| 2013/0014375 | A1 | 1/2013 | Hempstead et al. |
| 2014/0135804 | A1 | 5/2014 | Weisenburgh, II et al. |
| 2016/0296274 | A1 | 10/2016 | Mensch et al. |
| 2017/0290574 | A1 | 10/2017 | Batchelor et al. |

FOREIGN PATENT DOCUMENTS

| | | |
|---|---|---|
| CN | 107530126 A | 1/2018 |
| CN | 107530126 B | 12/2020 |
| EP | 2449983 A1 | 5/2012 |
| EP | 3280340 A2 | 2/2018 |
| EP | 3280340 B1 | 1/2021 |
| JP | H09510113 A | 10/1997 |
| JP | 2012501736 A | 1/2012 |
| JP | 2018510737 A | 4/2018 |
| JP | 6472538 B2 | 2/2019 |
| WO | WO-2016164266 A2 | 10/2016 |
| WO | 2017177098 A | 10/2017 |

OTHER PUBLICATIONS

Japanese Office Action for Japanese Patent Application No. 2017-553099 dated Jul. 31, 2018.
Potentially Related U.S. Appl. No. 15/481,841, filed Apr. 7, 2017 Published as US 2017/0290574.
"U.S. Appl. No. 15/088,655, 312 Amendment filed May 16, 2019", 7 pgs.
"U.S. Appl. No. 15/088,655, Examiner Interview Summary dated Feb. 13, 2019", 3 pgs.
"U.S. Appl. No. 15/088,655, Examiner Interview Summary dated Sep. 5, 2018", 3 pgs.
"U.S. Appl. No. 15/088,655, Final Office Action dated Dec. 26, 2018", 17 pgs.
"U.S. Appl. No. 15/088,655, Non Final Office Action dated Jun. 14, 2018", 14 pgs.
"U.S. Appl. No. 15/088,655, Notice of Allowance dated Mar. 7, 2019", 6 pgs.
"U.S. Appl. No. 15/088,655, PTO Response to Rule 312 Communication dated Jul. 1, 2019", 2 pgs.
"U.S. Appl. No. 15/088,655, Response filed Feb. 7, 2019 to Final Office Action dated Dec. 26, 2018", 11 pgs.
"U.S. Appl. No. 15/088,655, Response filed Sep. 11, 2018 to Non Final Office Action dated Jun. 14, 2018", 10 pgs.
"Chinese Application Serial No. 201680020739.6, Office Action dated May 8, 2020", w/ English Translation, 11 pgs.
"Chinese Application Serial No. 201680020739.6, Response filed Jul. 17, 2020 to Office Action dated May 8, 2020", w/ English Claims, 19 pgs.
"Chinese Application Serial No. 201680020739.6, Response filed Dec. 9, 2019 to Office Action dated Jul. 25, 2019", w/ English Claims, 16 pgs.
"European Application Serial No. 16719587.4, Communication Pursuant to Article 94(3) EPC dated Jan. 2, 2020", 6 pgs.
"European Application Serial No. 16719587.4, Response filed Apr. 29, 2020 to Communication Pursuant to Article 94(3) EPC dated Jan. 2, 2020", 4 pgs.
"European Application Serial No. 16719587.4, Response to Communication pursuant to Rules 161(1) and 162 EPC filed May 4, 2018", 29 pgs.
"international Application Serial No. PCT/US2016/025566, International Preliminary Report on Patentability dated Oct. 19, 2017", 8 pgs.
"International Application Serial No. PCT/US2016/025566, International Search Report dated Oct. 11, 2016", 3 pgs.
"International Application Serial No. PCT/US2016/025566, Written Opinion dated Oct. 11, 2016", 6 pgs.
"Japanese Application Serial No. 2017-553099, Response filed Oct. 29, 2018 to Office Action dated Jul. 31, 2018", W/English Translation, 16 pgs.

\* cited by examiner

MEDICAL FORCEPS WITH OFFSET TEETH

FIELD

These teachings relate generally to an instrument, and more specifically to a medical forceps for gripping a feature of interest without damaging the feature of interest.

BACKGROUND

Generally, forceps are a plier-like instrument having opposing jaws and teeth for effecting a feature or item of interest such as a vessel or tissue. Effecting may mean for example, that a feature of interest is gripped, manipulated, pulled, and/or constricted with the jaws and/or teeth. While aggressive tooth patterns may be desirable for reliably gripping and manipulating a vessel or tissue between the jaws, an aggressive tooth pattern may undesirably tear or otherwise damage the gipped vessel or tissue. As can be imagined, a torn or damaged vessel or tissue may cause pain, discomfort, and/or scarring to a patient; may cause increased blood loss; the duration of the medical procedure may be extended; and/or additional complications may occur. While a less aggressive tooth pattern may prevent a vessel or tissue from becoming torn or otherwise damaged, a less aggressive tooth pattern may undesirably cause a surgeon to struggle to manipulate the vessel or tissue, especially a thicker vessel or tissue section.

Electrosurgical forceps are a plier-like instrument having opposing jaws and teeth for effecting a vessel or tissue; however, one or both of the jaws are provided with an electrosurgical signal for coagulating the vessel or tissue between the jaws. While aggressive tooth patterns may be desired to reliably grip and manipulate a vessel or tissue, an aggressive tooth pattern may tear or otherwise damage a tissue or vessel, which may cause the opposing jaws to contact each other and cause an electrical short circuit and/or electrical fault.

U.S. Pat. Nos. 4,784,136, 5,059,214, 6,162,220, and 7,887,535 appear to describe exemplary instruments that may be used as a medical instrument or forceps, all of which are hereby incorporated by reference herein. However, the aforementioned devices do not appear to remedy the above described problems. Thus, it may be desirable to provide an instrument or forceps that have a suitable tooth pattern that can securely grip, manipulate, pull and/or constrict a vessel or tissue, while reducing or preventing the vessel or tissue from tearing, ripping, and/or otherwise becoming damaging when gripped.

SUMMARY present teachings provide a forceps including a gripping assembly. The gripping assembly includes an upper jaw and a lower jaw. The upper jaw includes a proximal end and a distal end. The upper jaw includes an upper tooth having an upper proximally facing canted tooth surface and an upper distally facing canted tooth surface. The lower jaw includes a proximal end and a distal end. The lower jaw includes a socket having a lower distally facing canted socket surface and a lower proximally facing socket surface. The upper jaw, the lower jaw, or both are moveable so that the gripping assembly moves between an open position and a gripping position. In the gripping position, a gap is defined between the upper distally facing canted tooth surface and the lower proximally facing socket surface.

The present teachings also provide a medical instrument including a forceps. The forceps include a first jaw and a second jaw. The first jaw including a first tooth. The first tooth has a first proximally facing canted tooth surface and a first distally facing canted tooth surface. The second jaw includes a second tooth having a second proximally facing tooth surface; and a second distally facing canted tooth surface. In a gripping position, the first proximally facing canted tooth surface generally opposes the second distally facing canted tooth surface. In the gripping position, the first distally facing canted tooth surface generally opposes the second proximally facing tooth surface so that a gap is defined therebetween. A width of the gap increases from an upper portion of the second proximally facing tooth surface to a lower portion of the second proximally facing tooth surface.

The present teachings further provide forceps jaws having a tooth pattern that can securely grip, pull, manipulate and/or constrict a vessel or tissue, while also reducing or preventing the vessel or tissue from tearing, ripping, and/or otherwise becoming damaging.

Even further yet, the present teachings provide a tooth pattern that is offset so that opposing teeth in each of the jaws are restricted from ripping, tearing and/or otherwise extending through a tissue or vessel.

Still further yet, the present teachings provide a tooth pattern for electrosurgical forceps that can securely grip a tissue or vessel without ripping or tearing the tissue or vessel to prevent a short circuit or an electrical fault from occurring.

The present teachings also provide a tooth pattern that includes one jaw with least one vertical gripping surface while the opposing jaw does not include a matching or corresponding vertical gripping surface to prevent vessel or tissue shearing.

Also provided is a tooth pattern that includes one jaw with at least one canted or non-vertical tooth surface and an opposing second jaw including at least one matching or corresponding canted or non-vertical tooth surface so that compressive stresses on a vessel or tissue can be distributed when gripped with the forceps.

The present teachings also provide forceps, electrosurgical forceps, or both, where one or more of the jaws that do not shear tissue or a feature of interest gripped or held between the jaws; rather, the jaws support a high push force, pull force, retraction force, or a combination thereof on the tissue or feature of interest.

DETAILED DESCRIPTION

Figure 1:
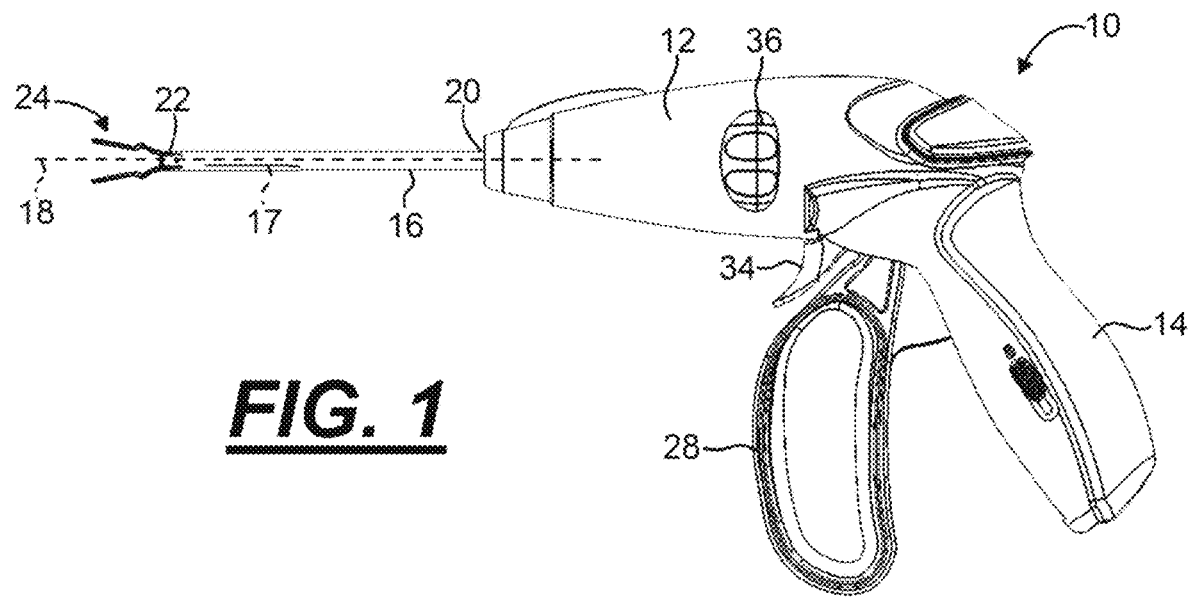
FIG. 1 is a side view of an instrument including a gripping assembly and a cutting assembly.

This Application is a continuation of U.S. patent application Ser. No. 15/088,655, titled "Medical Forceps with Offset Teeth," filed Apr. 1, 2016, now issued U.S. Pat. No. 10,368,940, which claims priority to U.S. Provisional Application No. 62/145,620 filed on Apr. 10, 2015, each of which is hereby incorporated by reference herein for all purposes.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting, of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide an instrument. The instrument may be a medical instrument or medical device. The instrument may be a medical forceps. The instrument may be used to effect an item or feature of interest. For example, the instrument may be used to manipulate, grip, pull, constrict, cut, transect, coagulate, seal, or a combination thereof an item or feature of interest. The item or feature of interest may include, but is not limited to: one or more parts of a body, one or more anatomical features, one or more vessels, tissues, veins, arteries, the like, or a combination thereof. The instrument may be any forceps that may be used in any procedure or surgery, such as laparoscopic surgery.

The instrument may be used with or without power. That is, one or more electric currents, therapies, and/or signals may be passed through the instrument so that the instrument can be used in electrosurgery. The current, therapy, and/or signal can be used to electrically effect an item or feature of interest. For example, the current, therapy, and/or signal can be suitable to coagulate, cauterize, cut, or a combination thereof a feature of interest. For example, a current, therapy, and/or signal may be passed from or through one jaw to another jaw. For example, a current, therapy, and/or signal may be passed from or through one jaw to a remote pad or electrode. For example, a current, therapy, and/or signal may be passed from or through one jaw to another jaw while another current, therapy, and/or signal may be passed from or through one jaw to a remote pad or electrode. The instrument can be used with monopolar current, therapies, and/or signals, bipolar current therapies, and/or signals, a blended monopolar and bipolar therapy, current, and/or signal, or a combination thereof.

The instrument may include a body. The body may function to house or contain the cutting assembly, the gripping as and/or the parts needed to move or actuate the cutting assembly; the gripping assembly, or both. The body may be made of or fabricated from any material suitable for use in medical procedures.

The body may include one or more gripping portions. The one or more gripping portions may function to be held, gripped, manipulated, or a combination thereof by a user. The one or more gripping portions may be configured for a user to grip with one hand or with two hands. The one or more gripping portions may be configured so that a user can grip the instrument while also being able to reach and actuate one or more controls (e.g., triggers, rotation wheels, etc.).

The instrument, the body, or both may include one or more controls. The one or more controls may function to move, rotate, actuate, open, close, reciprocate, or a combination thereof the introducer, the gripping assembly, the cutting assembly, or a combination thereof relative to a gripping axis, a introducer axis, a cutting axis, the body, the floor, the anatomy, the surgeon, or a combination thereof. The one or more controls may move the gripping assembly between an open position, a closed or gripping position, or a position therebetween. The one or more controls may function to apply one or more currents, therapies, and/or signals from a source, such as a generator, to the instrument, the gripping assembly, the cutting assembly, or a combination thereof.

The one or more controls may be or may include one or more triggers, wheels, levers, buttons, knobs, the like, or a combination thereof. The one or more controls may include mechanical components, electrical components, electro-mechanical components or a combination thereof to move or actuate the introducer, the gripping assembly, the cutting assembly, or a combination thereof. The one or more controls may be directly connected to the gripping assembly, the cutting assembly, or both, or may be connected thereto via one or more support rods, one or more camming sections, or a combination thereof.

The instrument, the body, or both may include one or more introducers. The introducer may function to house, contain, actuate, move, retract, expand, and/or protect the gripping assembly, the cutting assembly, or both. The introducer may extend along a longitudinal axis, between a proximal end and a distal end. The distal end of the introducer may be configured to extend towards or into a patient, while a proximal end of the introducer may be configured to engage the body of the medical forceps.

The introducer may be moveable relative to the jaw assembly, the body, the anatomy, a surgeon, or a combination thereof. The introducer may be axially moveable along an introducer axis. The introducer may be moveable (e.g., proximally or distally) relative to the body so that the introducer either engages or disengages the camming sections on the gripping assembly so that the gripping assembly can be correspondingly moved into a closed position or an open position. The introducer may also be rotated around its own longitudinal axis. The introducer may be static relative to the body (e.g., not rotatable, not axially rotatable, or both).

The introducer may be any device or combination of devices that may be used to extend the cutting assembly, the gripping assembly, or both towards or into a patient. The introducer may be made from a material that is rigid, flexible, or both. The introducer may be generally linear, or may include one or more curves, bends. The introducer may be hollow. The introducer may be tubular shaped. The introducer may be a cannula. The introducer may include a cross section that may be square, round, oval, irregular, or any shape. The introducer may include a cross-section that may be consistent throughout, or the cross-section may vary, slope, change, and/or taper between the proximal and distal ends thereof. The introducer may assist in moving, rotating, and/or actuating the gripping assembly, the cutting assembly, or both.

The introducer may include one or more inner portions. The inner portion may function to house, contain, actuate, support, contact, move, retract, expand and/or protect the gripping assembly, the cutting assembly, or both. The inner portion of the introducer may be any size or diameter so that the cutting assembly, the griping assembly, or both may extend there through. The cutting assembly, the griping assembly, or both may be moveable into and out of the introducer (i.e., along the longitudinal axis of the one or more introducers), rotationally within the one or more introducers, or both. The size of the inner portion may be sufficient so that one or more camming sections that extend from the one or more opposing jaws (i.e., the upper jaw, the lower jaw, or both), the one or more cutting blades or cutting assemblies, or both can be engaged therewith. The one or more inner portions may include a diameter that may be about 1 mm or more, preferably 3 mm or more, more preferably 5 mm or more. The one or more inner portions may include a diameter that may be about 20 mm or less, preferably about 15 mm or less, or more preferably about 10 mm or less.

During use, engaging the one or more camming sections with the inner portion may force one or both of the opposing laws to bias, pivot and/or move towards one another into a gripping position and create a gripping force therebetween. Engaging the one or more camming sections may be accomplished by moving the gripping assembly proximally or distally relative to the body, moving the tubular member proximally or distally relative to the body, or both. During use, disengaging the one or more camming sections from contact with the inner portion may release one or both of the jaws move, resiliently move, flex, and/or bias away from one another into an open position to release the gripping force. The one or more camming sections may also be engaged by other forms of pressure, for example, by applying finger pressure in the case of tweezers to move the jaws into a gripping position. Accordingly, by releasing the finger pressure, the camming sections can be disengaged so that the jaws move into an open position.

The instrument may include one or more cutting assemblies. The cutting assembly may be any feature that may perform a cutting function. The cutting function may be performed on a feature of interest that located is near the jaws. The cutting function may be performed on a feature of interest that is held, positioned, and/or gripped between the jaws. The cutting assembly may rotate independently of, or together with, the introducer, the gripping assembly, or both. The cutting assembly may be extended beyond a distal end of the instrument, the gripping assembly, or both when the gripping assembly is in a gripping position, an open position, or in a position therebetween. The cutting assembly may be retracted to a position within the gripping assembly when the gripping assembly is in a gripping position, an open position, or in a position therebetween. The cutting assembly may be moved or actuated with one of the controls.

The cutting assembly may include one or more cutting blades. The cutting blade may function to effect an item or feature of interest. For example, the cutting blade may function to cut, transect, cauterize, or a combination thereof a feature or area of interest. The one or more cutting blades may be any cutting tool, blade, and/or member that may be used in or during a medical procedure. The cutting blade may be rotated, extended, and/or retracted through the one or more introducers, the gripping assembly, or both. The one or more cutting blades may be selectively reciprocated to cut a feature of interest that is located near the gripping assembly, and/or located, gripped, or placed between the jaws. The cutting blade may be rotated, extended, retracted and/or reciprocated through the introducer, the gripping assembly, or both when the gripping assembly is in a closed position, an open position, a position in-between, or a combination thereof. The cutting blade may be any shape that may generally fit inside the inner or hollow portion of the introducer and may extend into the gap formed between the two opposing jaws. The distal end of the cutting blade, a bottom edge, a top edge, or a combination thereof may have a sharp edge. The cutting blade may include one or more sharp or serrated teeth or blades. The cutting blade may be coupled directly to one of the controls (e.g., trigger, rotation wheel, etc.), or may be coupled thereto via one or more support rods, camming sections, or both so that a user can move the one or more cutting blades. One or more, currents, signals, and/or therapies may be supplied to the one or more cutting blades so that the blade can function as an electrosurgical blade. The one or more currents, signals, and/or therapies may be supplied to the cutting blade so that the blade can function as a monopolar blade, a bi-polar blade, or both.

The instrument may include one or more gripping assemblies. The gripping assembly may be moved between a closed or gripping position and an open position.

In the open position, the gripping assembly may function to release a gripping force; apply less force or pressure onto a feature of interest than in the gripping position; or both. In the open position, one or more teeth or surfaces of the teeth may be free from contacting one another; one or more teeth or surfaces of the teeth may be in contact with one another, or a combination thereof. In the open position, one or more gaps may be formed between one or more corresponding tooth and/or socket surfaces; one or more gaps may be formed between peaks and corresponding valleys; one or more corresponding tooth and/or socket surfaces may be in contact; one or more peaks and corresponding valleys may be in contact; or a combination thereof.

In the closed or gripping position, the gripping assembly may function to create and/or maintain a gripping force; grip a feature of interest; apply a force or pressure onto a feature of interest that is greater than a force or pressure applied when the gripping assembly is in an open position, or a combination thereof. In the closed or gripping position, one or more gaps may be formed between one or more corresponding tooth and/or socket surfaces; one or more gaps may be formed between peaks and corresponding valleys; one or more corresponding tooth and/or socket surfaces may be in contact; one or more peaks and corresponding valleys may be in contact; or a combination thereof.

The gripping assembly may generally include one or more jaws, or preferably two or more jaws. One or both of the jaws may be biased, flexed, moved, pivoted, and/or rotated towards one another to create a gripping force, to grip or hold a feature of interest. One or both of the jaws may be biased, flexed, moved, pivoted, relaxed and/or rotated away from each other to release a gripping force, to release a previously gripped feature of interest, or both. The jaws may be any structure(s) or member(s) that may allow for one jaw to be static and one jaw to be movable; for both jaws to be moveable, or any combination thereof.

Depending on an orientation of the instrument, the two or more jaws may be labeled as an upper jaw and a lower jaw;

a first jaw and a second jaw; a left jaw and a right jaw; a primary jaw and a secondary jaw; the like; or a combination thereof.

One or more of the jaws may include a center channel (i.e., an upper center channel, a lower center channel, or both). The center channel may allow for a cutting assembly, a cutting blade or instrument, another working function or assembly, or a combination thereof to be positioned, actuated, extended, retracted, reciprocated, moved, rotated, or a combination thereof while the jaws are in a closed position, an open position, or in a position therebetween. The one or more center channels may be any shape and size so that a cutting assembly or cutting blade, a functional element, a surgical instrument, or a combination thereof may extend into or between the one or more jaws, into or between the center channels, or both. One or more of the jaws may be free of a center channel.

One or more of the jaws may be made of a material that is at least partially flexible, resilient, rigid, stainless, plastically deformable, or a combination thereof. One or more of the jaws may be made of a material that conducts electricity. One or more of the jaws may apply electricity, current, a therapy current, or a combination thereof to a feature of interest. A gripping portion of one or more of the jaws may have a surface, an area, or a portion for gripping, holding, manipulating, and/or pulling a feature of interest. For instance, one or more gripping portions or surfaces may be at least partially smooth, flat, contoured, serrated, textured, horizontal, toothed, vertical, planar, canted, rolling, irregular, knurled, grit blasted, or a combination thereof. The grit blast may be a 60 grit blast or lower, a 400 grit blast or higher, or a grit blast in between 60 grit and 400 grit. The one or more gripping portions or jaws may include one or more ridges, teeth, mouse teeth, gaps, openings, of a combination thereof. One or more of the jaws may be generally U-shaped.

One or more of the jaws may have one or more camming sections. The one or more camming sections may be laterally extending at the proximal end of the jaws that protrude out from the distal end of the introducer. At least a portion of the camming sections are wider than the inner portion of the introducer so that axial movement of the hollow tube, the jaw support rods, or both can provide for the tubular member to contact and/or engage the camming sections and thus bias one or more of the jaws to close the jaws and create a gripping force. Axial movement of the hollow tube, the jaw support rods, or both can provide for the tubular portion to disengage the camming sections and thus allow one or both of the jaws to move, bias, flex, relax, and/or pivot away from another to release the gripping force. As discussed above, the camming section can also be engaged by applying other forms of pressure or force thereon, such as finger pressure.

The one or more camming sections may be any portion of the jaw, support rods, or both. For example, the one or more camming sections may be one or more raised portions, arcuate portions, thicker portions or sections, ramps, biasing members, or a combination thereof. The one or more camming sections may be constructed from the same material as the jaws or may be constructed from a different material. For example, the one or more camming sections may be made of a resilient or flexible material; may be a living hinge (e.g., comprise one or more thinned out areas or channels); or a combination thereof.

The proximal end of one or more of the jaws may be attached to a jaw support rod. The jaw support rods may assist in creating a gripping force between the two opposing jaws. The jaw support rods may provide support to one or more jaws extending through the introducer. The jaw support rods may be generally any shape that may perform the recited functions. The jaw support rods may be flexible, rigid, electrically conductive, elastically deformable, or a combination thereof. The jaw support rods may extend through the introducer at/from the distal end of the introducer, at/from the proximal end of the introducer, or a combination thereof. The jaw support rods may be connected to one or more of the controls on the hand piece to move and/or actuate the gripping assembly.

The one or more upper jaws may function to cooperate with the one or more lower jaws to create or perform a gripping function. The upper jaw may function to perform a gripping function so that one or more features or items of interest can be effected. The upper jaw may function to perform a gripping function without tearing or otherwise damaging the anatomical feature gripped. Preferably, the upper jaw does not shear tissue or a feature of interest gripped or held between the jaws; rather, the jaws support a high push force, pull force, retraction force, or a combination thereof on the tissue or feature of interest. The upper jaw may be electrically conductive.

The upper jaw may have a U-shape (e.g., a slot in the jaw), or the upper jaw may be substantially solid (e.g., without a slot). The upper jaw may include one jaw portion, or preferably may include two jaw portions (i.e., a first jaw portion and a second jaw portion, and a channel therebetween). The two jaw portions may extend generally parallel to one another. The upper jaw may include a center channel or opening between two or more jaw portions (i.e., an upper center channel). The upper jaw may be open at a distal end thereof, or may include a radius or connecting portion connecting the two opposing jaw portions. The connecting portion, the distal end, or both may be flat, curved, arcuate, pointed, or a combination thereof.

The upper jaw may be moveable relative to the lower jaw while the lower jaw is static. The lower jaw may be moveable relative to the upper jaw while the lower jaw is static. The upper jaw may be moveable relative to a lower jaw that is moveable relative to the upper jaw.

The one or more upper jaws, jaw portions, gripping portions, or a combination thereof may include one or more upper teeth. The one or more upper teeth may function to cooperate with the one or more lower jaws, lower teeth, lower sockets, upper sockets, or a combination thereof to perform a gripping function. The one or more upper teeth may function to perform a gripping function so that one or more features or items of interest can be cut, transected, coagulated, gripped, manipulated, pulled, repositioned, or a combination thereof.

The one or more upper teeth may be fabricated from any material that is sufficient for use in medical procedures to securely grip, manipulate, hold, move, or, a combination thereof an item or feature of interest, such as a vessel, tissue or both. The one or more upper teeth may be fabricated from a material that may conduct electricity so that a therapy current can be applied to the vessel or tissue. The one or more upper teeth may be generally triangle-shaped, square-shaped, rounded, oval, tear-drop shaped, irregularly-shaped, or a combination thereof.

The one or more upper teeth or surfaces of the one or more upper teeth may be restricted or prevented from contacting one or more of the lower teeth, the one or more surfaces of the lower teeth, the one or more, surfaces of the lower sockets, or a combination thereof in the closed position, the open position, or both. The one or more upper teeth or surfaces of the one or more upper teeth may contact one or more of the lower teeth, the one or more surfaces of the lower teeth, the one or more surfaces of the lower sockets, or a combination thereof in the closed position, the open position.

The one or more upper teeth may include one or more upper proximal facing tooth surfaces and one or more upper distal facing tooth surfaces. One or more of the upper proximal facing tooth surfaces, upper distal facing tooth surfaces, or both may be linear, vertical, angled, canted, arcuate, irregular, or a combination thereof relative to an axis or feature. The axis may be a longitudinal axis that extends through the peaks of the one or more upper teeth, a longitudinal axis extending through the peaks of the one or more lower teeth, a longitudinal axis of the introducer, the longitudinal axis of the one or mare jaws, or a combination thereof. The feature may be the body, the anatomy, the ground, a surgeon, a patient, or a combination thereof. For example, the one or more upper proximal facing tooth surfaces may face generally towards a proximal end of the instrument, and the one or more distal facing tooth surfaces may face generally towards a distal end of the instrument, or vice versa.

The one or more upper proximally facing tooth surfaces may form an angle relative to an axis, that may be less than about 180 degrees, about 135 degrees or less, about 90 degrees or less, about 75 degrees or less, about 45 degrees or less, about 30 degrees or less, about 15 degrees or, less, or a combination thereof. The one or more upper distally facing tooth surfaces may form an angle relative an axis that may be less than about 180 degrees, about 135 degrees or less, about 90 degrees or less, about 75 degrees or less, about 45 degrees or less, about 30 degrees or less, about 15 degrees or less, or a combination thereof.

The one or more upper teeth may include a peak or an upper peak between corresponding upper proximal and distal tooth surfaces. One or more upper peaks may be rounded, flattened, pointed, irregular, angled, sharp, serrated, or a combination thereof. A gap may be defined an upper peak and a corresponding socket or valley. The peak may contact a corresponding socket or valley. An axis may extend through one or more of the upper peaks located on the same jaw portion, which may be the same as, parallel to, similar to, or angled relative to a longitudinal axis extending through the one or more introducers, jaw members, or both. An axis may extend through one or more corresponding upper peaks on opposing jaw portions and may form an angle relative to a longitudinal axis extending through the one or more introducers, jaw members, or both. For example, the angle may be less than about 180 degrees, about 160 degrees or less, about 135 degrees or less, about 90 degrees or less, about 75 degrees or less, about 45 degrees or less, about 30 degrees or less, about 15 degrees or less, or a combination thereof.

The position or location of the one or more upper peaks (i.e., the height amplitude of the one or more upper teeth) may be the same, or may vary along the length of the one or more upper jaws. In other words, the position, height, and/or amplitude of the one or more upper teeth or upper peaks at a proximal end of the upper jaw relative to upper teeth and/or peaks at or near a distal end of the upper jaw may be the same; higher or larger; lower or smaller, or a combination thereof. The upper peak, the height and/or amplitude of the upper teeth may be measured from a valley to a corresponding peak.

Between a pair of upper teeth, the one or more upper jaws may include one or more sockets or upper sockets. The upper sockets may include an upper proximally facing socket surface and an upper distally facing socket surface. One or more of the upper proximally facing socket surfaces and the upper distally facing socket surfaces may be linear, vertical, angled, canted, arcuate, irregular, or a combination thereof relative to an axis or feature. The axis may be a longitudinal axis that extends through the peaks of the one or more upper teeth, a longitudinal axis extending through the peaks of the one or more lower teeth, a longitudinal axis of the introducer, the longitudinal axis of the one or more jaws, or a combination thereof. The feature may be the body, the anatomy, the ground, a surgeon, a patient, or a combination thereof. For example, the upper proximally facing socket surfaces may face generally towards a proximal end of the instrument, and the upper distally facing socket surface may face generally towards a distal end of the instrument, or vice versa.

One or more of the upper proximally, facing socket surfaces and the upper distally facing socket surfaces may form an angle relative to an axis that may be less than about 180 degrees, about 135 degrees or less, about 90 degrees or less, about 75 degrees or less, about 45 degrees or less, about 30 degrees or less, about 15 degrees or less, or a combination thereof.

The one or more lower jaws may function to cooperate with the one or more upper jaws to perform a gripping function. The lower jaw may function to perform a gripping function so that one or more features or items of interest can be cut, transected, coagulated, gripped, manipulated, pulled, repositioned, or a combination thereof. The lower jaw may function to perform a gripping function without tearing or otherwise damaging the anatomical feature being gripped. Preferably. The lower jaw does not shear tissue or a feature of interest gripped or held between the jaws; rather, the jaws support a high push force, pull force, retraction force, or a combination thereof on the tissue or feature of interest.

The lower jaw may be substantially the same as the upper jaw. The lower jaw may include one jaw portion, or preferably two jaw portions (i.e., a first jaw portion and a second jaw portion). The one or more lower jaw portions may extend generally parallel to one another. The one or more lower jaws may include a center channel or opening between two or more jaw portions (i.e., an upper center channel). The lower jaw may be open at a distal end thereof, or may include a radius or a connecting portion connecting the two opposing jaw portions. The connecting portion, the distal end, or both may be flat, curved, arcuate, pointed, or a combination thereof. The lower jaw may be electrically conductive. The lower jaw may be in communication with a therapy current so that the one or more jaws can function as a monopolar jaw, a bipolar jaw, or both. The lower jaw, lower jaw portions, or both may include one or more lower teeth.

The one or more lower teeth may function to cooperate with the one or more upper jaws, upper teeth, upper sockets, or a combination thereof to perform a gripping function. The one or more lower teeth may function to perform a gripping function so that one or more features or items of interest can be cut, transected, coagulated, gripped, manipulated, pulled, repositioned, or a combination thereof. The one or more lower teeth may function to perform a gripping function without tearing or otherwise damaging an anatomical feature gripped or held between the jaws.

The one or more lower teeth or surfaces of the one or more lower teeth may be restricted or prevented from contacting one or more of the upper teeth, the one or more surfaces of the upper teeth, the one or more surfaces of the upper sockets, or a combination thereof in the closed position, the open position, or both. The one or more lower teeth or surfaces of the one or more lower teeth may contact one or more of the upper teeth, the one or more surfaces of the upper teeth, the one or more surfaces of the upper sockets, or a combination thereof in the closed position, the open position.

The one or more lower teeth may include one or more proximally facing tooth surfaces and one or more lower distally facing tooth surfaces. One or more of the lower proximally facing tooth surfaces and the lower distally facing tooth surfaces may be linear, vertical, angled, canted, arcuate, irregular, or a combination thereof relative to an axis or feature. The axis may be a longitudinal axis that extends through the peaks of the one or more lower teeth, the one or more lower teeth, a longitudinal axis of the introducer, the longitudinal axis of the one or more jaws, or a combination thereof. The feature may be the body, the anatomy, the ground, a surgeon, a patient, or a combination thereof. For example, one or more lower proximally facing tooth surfaces may face generally towards a proximal end of the instrument, and one or more lower distally facing tooth surfaces may face generally towards a distal end of the instrument, or vice versa.

One or more lower proximally facing tooth surfaces and one or more lower distally facing tooth surfaces may form an angle relative to an axis that may be less than about 180 degrees, about 135 degrees or less, about 90 degrees or less, about 75 degrees or less, about 45 degrees or less, about 30 degrees or less, about 15 degrees or less, or a combination thereof.

The one or more lower teeth may include a lower peak or valley between a corresponding lower proximal tooth surface and a lower distal tooth surface. The lower peak or valley may be rounded, flattened, pointed, irregular, angled, or a combination thereof. An axis may extend through one or more of the lower peaks or valley located on the same jaw portion, which may be same as, parallel to, or angled relative to a longitudinal axis of the one or more introducers, jaw members or both. An axis may extend through one or more corresponding lower peaks or valleys on opposing jaw portions, and may form an angle relative to a longitudinal axis extending through the one or more introducers, jaw members, or both. For example, the angle may be less than about 180 degrees, about 135 degrees or less, about 90 degrees or less, about 75 degrees or less, about 45 degrees or less, about 30 degrees or less, about 15 degrees or less, or a combination thereof.

The position or location of the one or more lower peaks or valleys (i.e., the height or amplitude of the one or more lower teeth) may be the same, or may vary along the one or more lower jaws. For example, the position, height, and/or amplitude of the one or more lower teeth or peaks at a proximal end of the lower jaw relative to other teeth or peaks near a distal end of the lower law may be the same; higher or larger; lower or smaller, or a combination thereof. The lower peak, or the height and/or amplitude of the lower teeth may be measured from a valley to a corresponding peak of a lower tooth.

One or more gaps may be formed between the one or more upper teeth and lower teeth. Gaps may be formed between one or more upper teeth surfaces, one or more of the lower teeth surfaces, one or more lower socket surfaces, one or more upper socket surfaces, or a combination thereof. The size of the gaps may be dictated by an angular position of the one or more upper tooth surfaces, the one or more lower tooth surfaces, the one or more upper or lower socket surfaces, or a combination thereof relative to an axis. In some configurations, a width of the gaps may be constant. In some configurations a width of a gap may increase or decrease between corresponding surfaces. For example, the width of a gap between an upper proximally facing tooth surface and a lower distally facing tooth surface may be constant or may vary (e.g., increase or decrease) from a peak of the lower tooth to a valley of an adjacent lower socket. The one or more gaps may allow or provide for tissue or a vessel to extend into so that compressive forces of the upper, jaw, the lower jaw, the upper teeth, the lower teeth, or a combination thereof do not tear or otherwise damage the tissue or vessel gripped or held therebetween. One or more gaps may be formed between corresponding peaks and valleys. In some configurations, no gaps are formed between corresponding upper and lower tooth surfaces, socket surfaces, etc. That is, an angular position of the upper teeth may sufficiency correspond to an angular position of the lower teeth line to line. In other words, a surface of the upper tooth may be line to line with a corresponding surface of lower tooth or lower socket.

In the following figures (FIGS. 1-12*b*), various gripping assemblies 24 are illustrated. As illustrated, the gripping assemblies 24 include one or more upper teeth 46, one or more lower teeth 62, and one or more lower sockets 60. The upper teeth 46 generally include an upper distally facing tooth surface 50 and a corresponding upper proximally facing tooth surface 48. The lower teeth 62 include a lower distally facing tooth surface 70 and a corresponding lower proximally facing tooth surface 68. The lower sockets 60 include a lower distally facing socket surface 64 and a lower proximally facing socket surface 66. It is understood that any of the tooth and socket surfaces, configurations, and/or arrangements illustrated and described in the FIGS. 1-12*b* can be combined with one another to form any desired gripping assembly 24. Moreover, as illustrated and described in the FIGS. 1-12*b*, some of the tooth and/or socket surfaces may be generally canted or generally vertical relative to an axis. The axis can be a longitudinal axis that extends through the upper jaw, the lower jaw, the gripping assembly, the introducer, or a combination thereof. The axis can be a longitudinal axis that extends between a proximal end and a distal end of the upper jaw, the lower jaw, the gripping assembly, the introducer, or a combination thereof. The axis can be a longitudinal axis that extends through adjacent peaks of the upper teeth or lower teeth, valleys of the sockets, etc.

FIG. 1 illustrates a medical device. The medical device may be a forceps 10. The forceps 10 includes a body 12 with a gripping portion 14. The forceps 10 includes an introducer 16 extending along a longitudinal axis 18 between a proximal end 20 and a distal end 22. The introducer 16 includes an inner portion 17. A gripping assembly 24 and a cutting assembly 26 (FIG. 2) are located at least partially within the inner portion 17 of the introducer 16. The gripping assembly 24 and/or the cutting assembly 26 are connected to one or more controls on the body 12 (trigger 28; trigger 34; and/or wheel 36).

Figure 2:
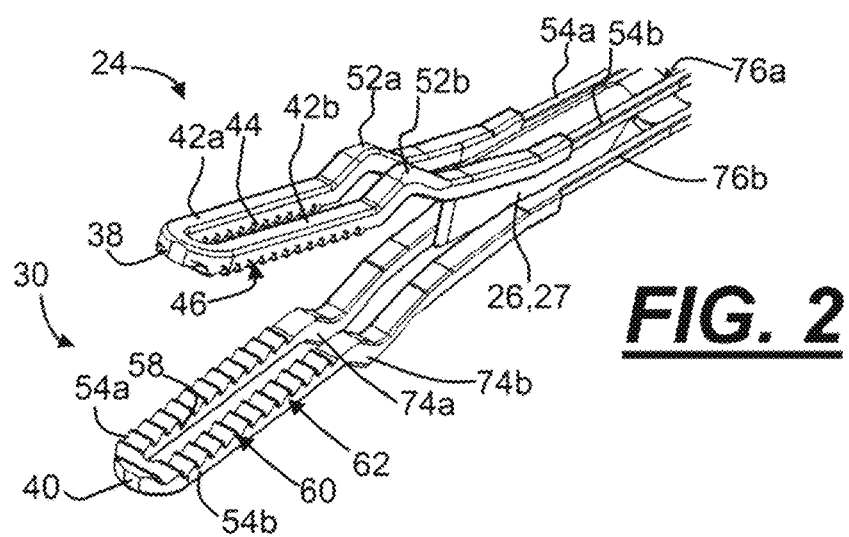
FIG. 2 is a partial perspective view of a gripping assembly and the cutting assembly.

FIG. 2 illustrates a gripping assembly 24. The gripping assembly 24 is illustrated in an open position 30. The gripping assembly 24 includes an upper jaw 38 and an opposing lower jaw 40. The upper jaw 38 includes a first jaw portion 42*a*, a second jaw portion 42*b*, and an upper center channel 44 defined therebetween. One or more upper teeth 46 extend from the first and second jaw portions 42*a*, 42*b*. Proximally extending from the first and second jaw portions 42*a*, 42*b* are respective upper camming sections 52*a*, 52*b*. Upper support rods 54*a*, 54*b* are located proximally to the respective upper camming sections 52*a*, 52*b*.

With continued reference to FIG. 2, the lower jaw 40 includes a third jaw portion 54a, a fourth jaw portion 54b, and a lower center channel 58 defined therebetween. One or more lower teeth 62 extend from the jaw portions 54a, 54b. A lower socket 60 is defined between a pair of lower teeth 62. The third and fourth jaw portions 54a, 54b also include respective lower camming sections 74a, 74b. Lower support rods 76a, 76b are proximally located to the lower camming sections 74a, 74b.

With continued reference to FIG. 2, the cutting assembly 26 includes a cutting blade 27. The cutting assembly 26 extends at least partially between the upper and lower jaws 38, 40 and the center channels 44, 58. The support rods 54a, 54b, 76a, 76b, and/or the cutting blade 27 are ultimately connected to one or more controls (e.g., trigger 28; trigger 34; and/or wheel 36; See FIG. 1) on the body 12.

Figure 3:
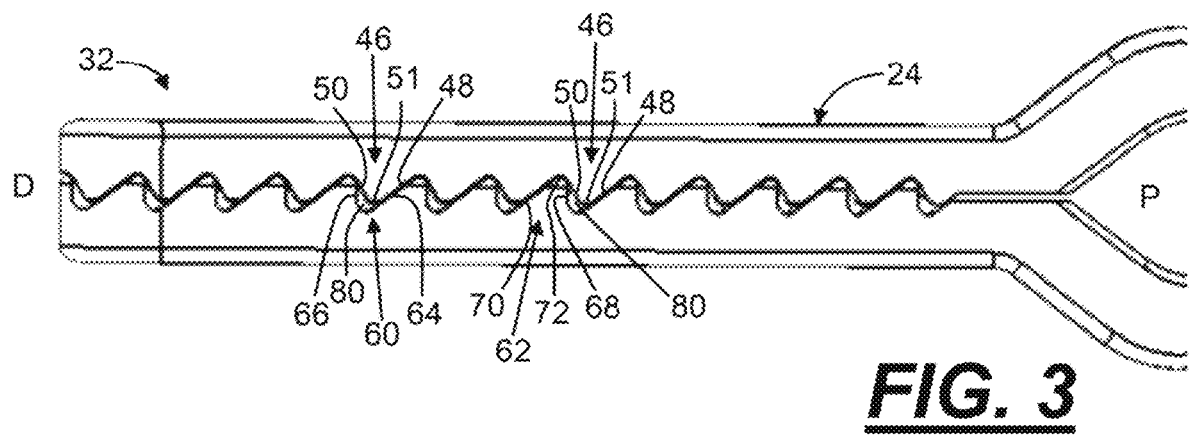
FIG. 3 is a partial side view of a gripping assembly.

FIG. 3 illustrates the gripping assembly 24. The gripping assembly 24 is illustrated in the gripping position 32. The gripping assembly 24 has a proximal end P and a distal end D. One or more of the upper teeth 46 include an upper proximally facing canted tooth surface 48 and an upper or second distally facing canted tooth surface 50. An upper peak 51 extends between corresponding upper proximally facing canted tooth surfaces 48 and upper or second distally facing canted tooth surfaces 50.

With continued reference to FIG. 3, one or more of the lower sockets 60 include a lower distally facing canted socket surface 64 and a lower proximally facing socket surface 66. The lower proximal facing socket surface 66 is illustrated generally vertical relative to a longitudinal axis of the jaw. A gap 80 is defined between the proximal facing socket surface 66 and a corresponding upper distally facing canted tooth surface 50.

With continued reference to FIG. 3, one or more of the lower teeth 62 include a lower proximally facing tooth surface 68 and a lower or first distally facing canted tooth surface 70. The lower proximally facing tooth surface 68 is illustrated generally vertical relative to a longitudinal axis (e.g., See exemplary axis at FIG. 4, reference numerals 56 or 72 and/or exemplary axis 18 at FIG. 1). A lower peak or valley 72 is defined between a lower proximally facing tooth surface 68 and a corresponding lower distally facing canted tooth surface 70. A gap 80 is defined between an upper distally facing canted tooth surface 50 and a corresponding lower proximally facing tooth surface 68.

Figure 4:
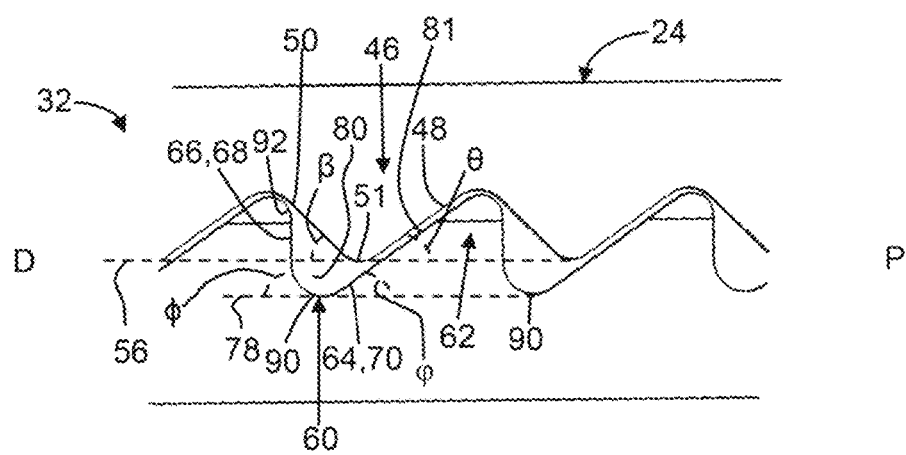
FIG. 4 is a partial side view of a gripping assembly.

FIG. 4 illustrates the gripping assembly 24 in the gripping position 32. The gripping assembly 24 has a proximal end P and a distal end D. One or more of the upper proximally facing canted tooth surfaces 48 have an angle θ relative to the longitudinal axis 56, which extends through adjacent peaks 51 of the upper teeth 46. One or more of the upper distally facing canted tooth surfaces 50 have an angle β relative to the longitudinal axis 56. One or both of the lower distally facing canted tooth surfaces 70 and the lower distally facing canted socket surfaces 64 have an angle φ relative to a longitudinal axis 78, which extends through one or more, valleys 90 of the lower socket 60. A valley 90 extends between a lower distally facing socket surface 64 and a corresponding lower proximally facing socket surface 66. One or more of the lower proximally facing socket surface 66 and/or the lower proximally facing tooth surface 68 have an angle φ relative to the longitudinal axis 78.

With continued reference to FIG. 4, a gap 80 is defined between an upper distally facing canted tooth surface 50 and a corresponding lower proximally facing tooth surface 68. A width of the gap 80 measured between the lower proximally facing tooth surface 68 and the upper distally facing tooth surface 50 increases from an upper portion 92 of the lower proximally facing tooth surfaces 68 to the valley 90.

With continued reference to FIG. 4, a gap 80 is also defined between the upper distally facing canted tooth surface 50 and the lower proximally facing socket surface 66. As illustrated, the width of the gap 80 increases from an upper portion 92 of the lower proximally facing socket surface 66 to the valley 90. The width of the gap 80 can be measured between the lower proximally facing socket surface 66 and the upper distally facing tooth surface 50.

With continued reference to FIG. 4, a gap 81 is defined between the upper proximally facing canted tooth surface 48 and the lower distally facing canted tooth surface 70. The gap 81 is also defined between the upper proximally facing canted tooth surface 48 and the lower distally facing canted socket surface 64. As illustrated, relative to axis 56 and/or 78, an angular position of the upper proximally facing canted tooth surface 48 is substantially the same as (i.e., sufficiently corresponds to) the angular position of the lower distally facing canted tooth surface 70. Relative to axis 56 and/or 78, an angular position of the upper proximally facing canted tooth surface 48 is substantially the same as (i.e., sufficiently corresponds to) an angular position of the lower distally facing canted socket surface 64.

Figure 5:
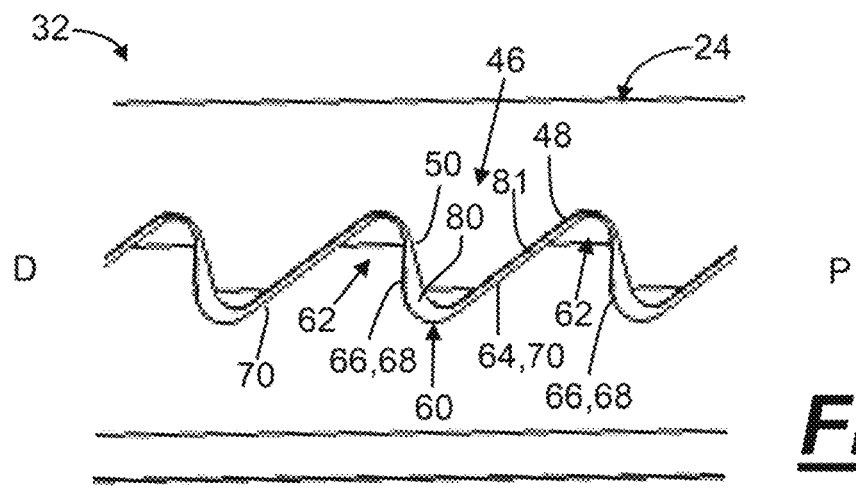
FIG. 5 is a partial side view of a gripping assembly.

FIG. 5 illustrates the gripping assembly 24 in the gripping position 32. The gripping assembly 24 has a proximal end P and a distal end D. The upper tooth 46 includes an upper proximally facing canted tooth surface 48 and an upper or second distally facing canted tooth surface 50. One or more of the sockets 60 include a lower distally facing canted socket surface 64 and a lower proximally facing socket surface 66. A gap 80 is defined between the proximal facing, socket surface 66 and the upper distally facing canted tooth surface 50. One, or more of the lower teeth 62 include a lower proximally facing tooth surface 68 and a lower or first distally facing canted tooth surface 70. The lower proximally facing tooth surface 68 that may be generally vertical relative to a longitudinal axis 56 (See FIG. 6, for example). A gap 80 is defined between corresponding upper distally facing canted tooth surfaces 50 and lower proximally facing tooth surface 68.

With continued reference to FIG. 5, a gap 81 is defined between the upper proximally facing canted tooth surface 48 and the lower distally facing canted tooth surface 70. The gap 81 is also defined between the upper proximally facing canted tooth surface 48 and the lower distally facing canted socket surface 64.

Figure 6:
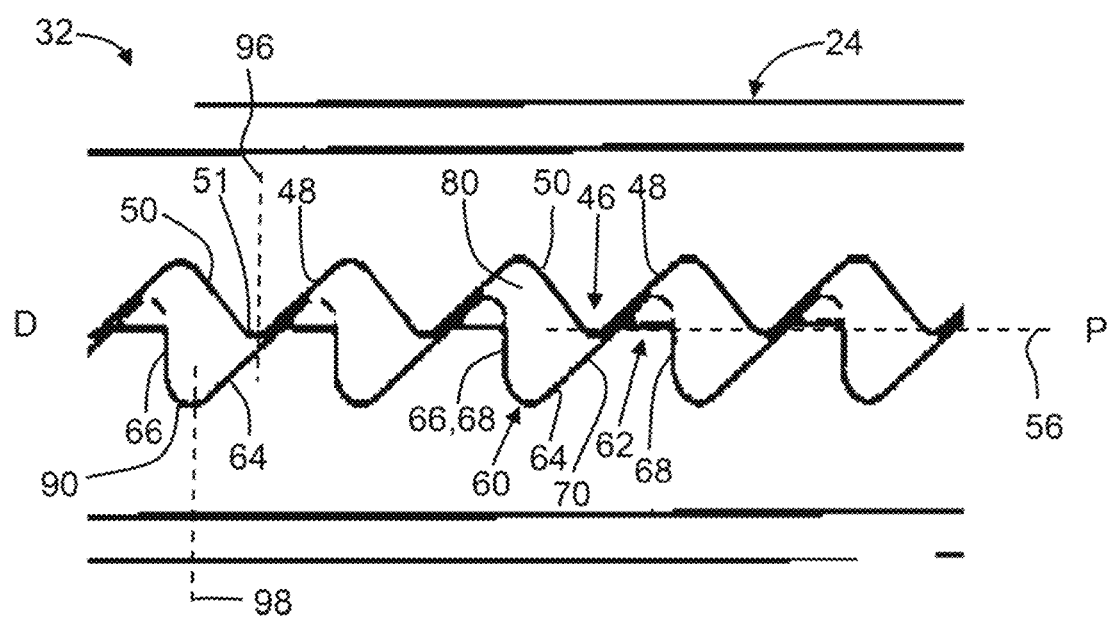
FIG. 6 is a partial side view of a gripping assembly.

FIG. 6 is a partial view of a gripping assembly 24 in the gripping position 32. The gripping assembly 24 has a proximal end P and a distal end D. The gripping assembly 24 includes upper teeth 46, lower teeth 62, and lower sockets 60. One or more of the upper teeth 46 include an upper proximally facing canted tooth surfaces 48 and an opposing upper distally facing canted tooth surface 50. One or more of the lower teeth 62 include a lower distally facing canted tooth surface 70 and a lower proximally facing tooth surface 68 that may be generally vertical (e.g., perpendicular) relative to an axis 56. One or more of the lower sockets 60 include a lower distally facing canted socket surface 64 and a corresponding lower proximally facing socket surface 66. The lower proximally facing socket surface 66 is generally vertical (e.g., perpendicular) relative to axis 56. A gap 80 is defined between the proximal facing socket surface 66 and the upper distally facing canted tooth surface 50. A gap 80 is defined between corresponding upper distally facing canted tooth surfaces 50 and lower proximally facing tooth surface 68.

With continued reference to FIG. 6, an axis 96 extends through an upper peak 51 defined between a corresponding upper distally facing tooth surface 50 and an upper proximally facing tooth surface 48. The axis 96 is offset relative to an axis 98 extending through a valley or lower peak 90. The valley or lower peak 90 is defined between lower distally facing canted socket surface 64 and a corresponding lower proximally facing socket surface 66. Axis 96 and 98 are generally parallel relative to one another, and both extend generally perpendicular to axis 56.

Figure 7:
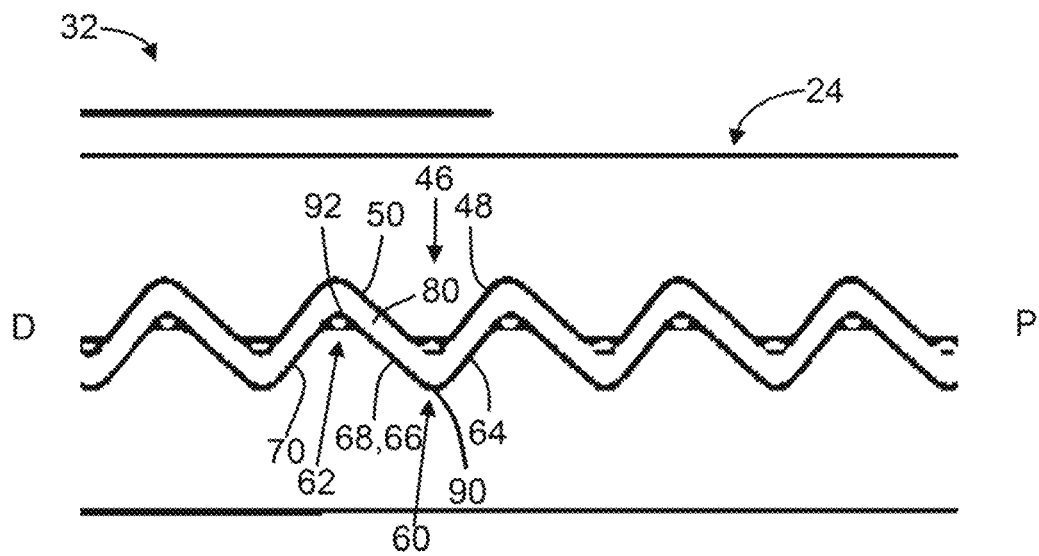
FIG. 7 is a partial side view of a gripping assembly.

FIG. 7 illustrates a partial view of a gripping assembly 24 in the gripping position 32. The gripping assembly 24 includes upper teeth 46, lower teeth 62, and lower sockets 60. The gripping assembly 24 has a proximal end P and a distal end D. One or more of the upper teeth 46 include an upper proximally facing canted tooth surfaces 48 and an opposing upper distally facing canted tooth surface 50. One or more of the lower teeth 62 include a lower distally facing canted tooth surface 70 and a lower proximally facing tooth surface 68. One or more of the lower sockets 60 include a lower distally facing canted socket surface 64 and a lower proximally facing socket surface 66.

With continued reference to FIG. 7, a gap 80 is defined between corresponding upper distally facing canted tooth surfaces 50 and lower proximally facing tooth surface 68. A width of the gap 80 measured between a corresponding upper distally facing canted tooth surface 50 and a lower proximally facing tooth surface 68 may be substantially the same or constant between an upper portion 92 of the lower proximally facing tooth surface 68 to the valley 90. The valley 90 extends between a corresponding lower proximally facing socket surface 66 and a lower distally facing socket surface 64.

Figure 8:
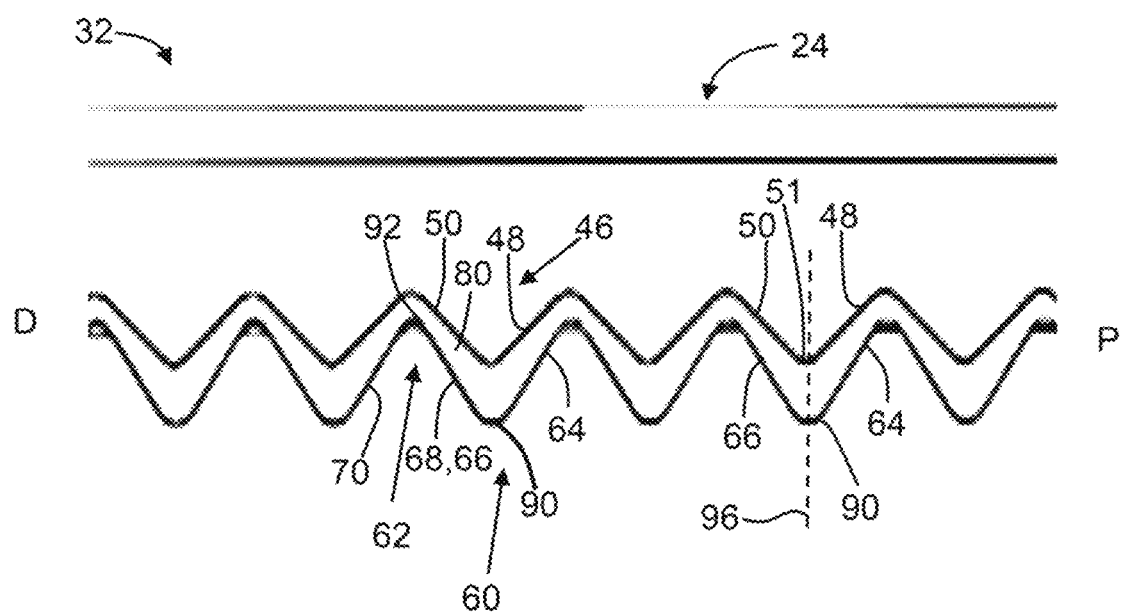
FIG. 8 is a partial side view of a gripping assembly.

FIG. 8 illustrates a partial view of a gripping assembly 24 in the gripping position 32. The gripping assembly 24 includes upper teeth 46, lower teeth 62, and sockets 60. The gripping assembly 24 has a proximal end P and a distal end D. One or more of the upper teeth 46 include an upper proximally facing canted tooth surfaces 48 and an opposing upper distally facing canted tooth surface 50. One or more of the lower teeth 62 include a lower distally facing canted tooth surface 70 and a lower proximally facing tooth surface 68. One or more of the lower sockets 60 include a lower distally facing canted socket surface 64 and a lower proximally facing socket surface 66.

With continued reference to FIG. 8, a gap 80 is defined between a corresponding upper distally facing canted tooth surface 50 and a lower proximally facing tooth surface 68. A width of the gap 80 measured between the lower proximally facing tooth surface 68 and the upper distally facing tooth surface 50 increases from an upper portion 92 of the lower proximally facing tooth surfaces 68 to the valley 90. The valley 90 extends between a corresponding lower proximally facing socket surfaces 66 and lower distally facing socket surfaces 64.

With continued reference to FIG. 8, a gap 80 is also defined between the upper distally facing canted tooth surface 50 and the lower proximally facing socket surface 66. As illustrated, the width of the gap 80 increases from an upper portion 92 of the lower proximally facing socket surface 66 to the valley 90. The width of the gap 80 can be measured between the lower proximally facing socket surface 66 and the upper distally facing tooth surface 50.

With continued reference to FIG. 8, an upper peak 51, which is defined between an upper distally facing tooth surface 50 and a corresponding upper proximally facing tooth surface 48, is substantially aligned along with the valley 90. In other words, axis 96 extends through the upper peak 51 and the valley 90. Axis 96 is substantially perpendicular to axis 56, 78 illustrated in FIG. 4, for example.

Figure 9:
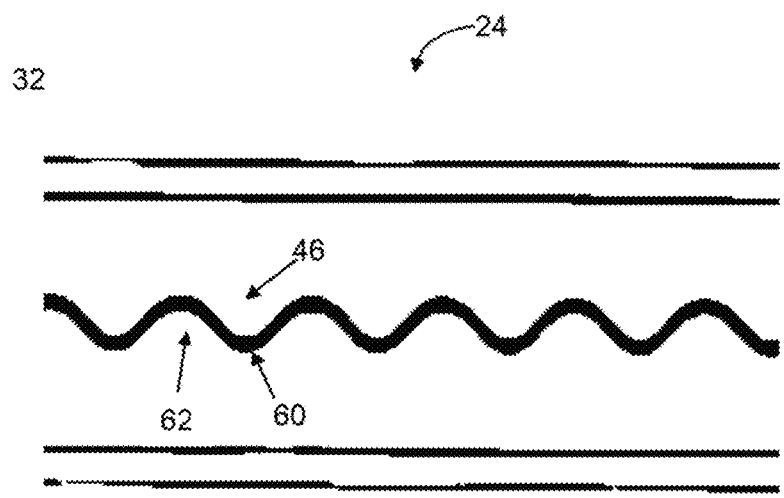
FIG. 9 is a partial side view of a gripping assembly.

FIG. 9 illustrates a partial view of a gripping assembly 24 in the gripping position 32. The gripping assembly 24 includes upper teeth 46, lower teeth 62, and sockets 60. The corresponding surfaces of the upper teeth 46, lower teeth 62, and sockets 60 may sufficiently correspond so that no gaps 80 are formed between the corresponding surfaces.

Figure 10:
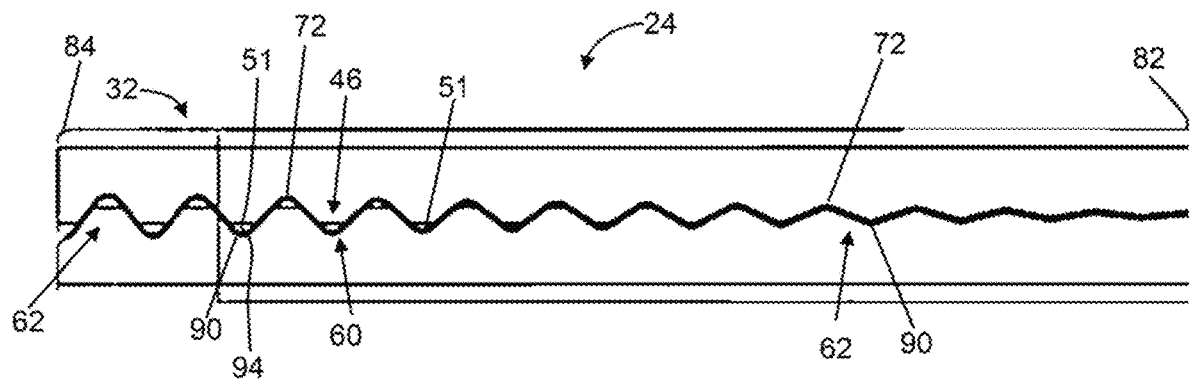
FIG. 10 is a partial side view of a gripping assembly.

FIG. 10 illustrates a partial view of a gripping assembly 24 in the gripping position 32. The gripping assembly 24 includes upper teeth 46, lower teeth 62, and lower sockets 60.

An amplitude and/or height of one or more of the lower teeth 62 may increase from the proximal end 82 to the distal end 84 of the jaws. In other words, near the distal end 84, when measured from a valley 90 to a corresponding peak 72, the lower teeth 62 may have an amplitude and/or height that is larger or greater than the amplitude and/or height of the lower teeth 62 near the proximal end 82. An amplitude and/or height of one or more of the upper teeth 46 may similarly correspondingly decrease from the distal end 84 to the proximal end 82. A gap 94 may be defined between some of the corresponding valleys 90 and peaks 51. As illustrated, the size of the gaps 94 may decrease between the distal end 84 and the proximal end 82.

Figure 11A:
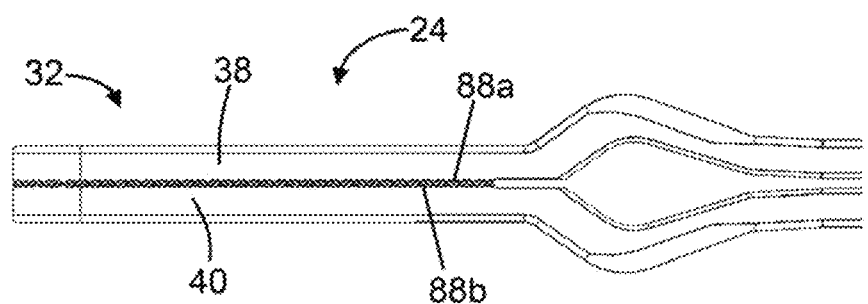
FIG. 11a is a partial side view of a gripping assembly.
Figure 11B:
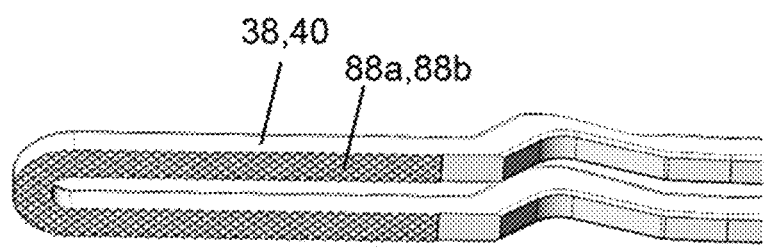
FIG. 11b is a partial perspective view of one of the jaws of a gripping assembly.

FIG. 11a illustrates a partial view of a gripping assembly 24 in the gripping position 32, and FIG. 11b illustrates a partial view of an upper jaw 38 or the lower jaw 40. Each upper and lower jaw 38, 40 includes a respective gripping portion 88a, 88b. In some configurations, one or both of the gripping portions 88a, 88b may include any of the teeth shown and described herein, and/or may be substantially flat or smooth, knurled, textured, or a combination thereof.

Figure 12A:
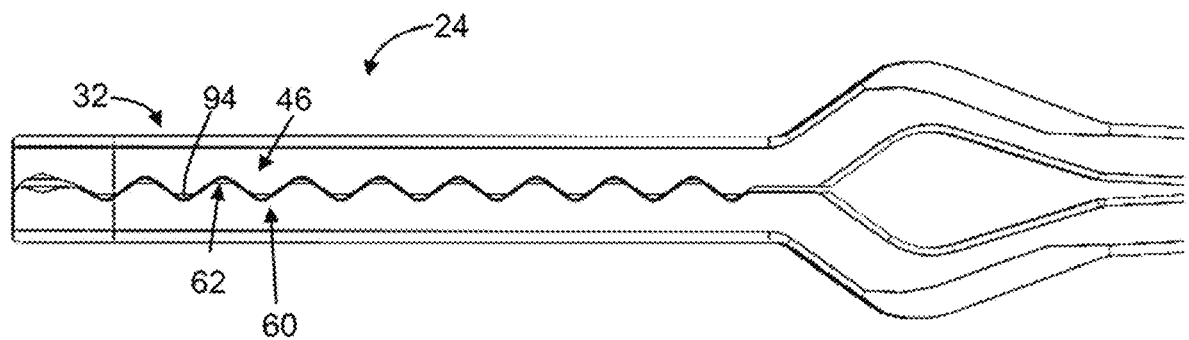
FIG. 12a is a partial side view of a gripping assembly.
Figure 12B:
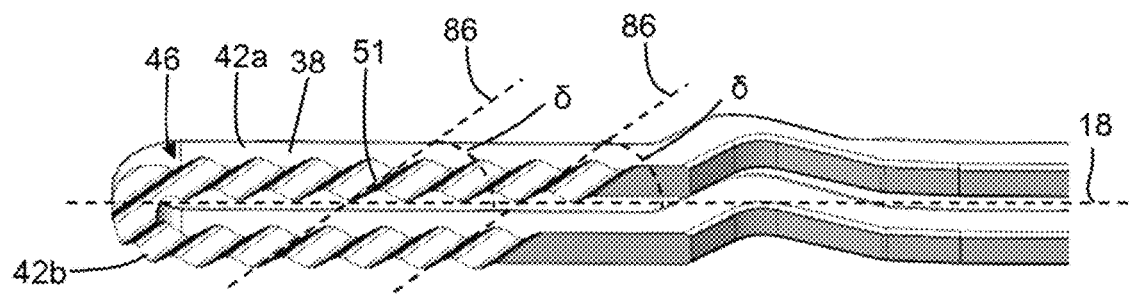
FIG. 12b is a partial perspective view of one of the jaws of a gripping assembly.

FIG. 12a illustrates a partial view of a gripping assembly 24 in the gripping position 32. The gripping assembly 24 includes upper teeth 46, lower teeth 62 and sockets 60. As perhaps best shown in FIG. 12b, the upper teeth 46 are angled relative to the longitudinal axis 18. The longitudinal axis 18 may extend through the introducer 16 (not shown; See FIG. 1), through the jaw, or a both. In other words, an axis 86 extending through corresponding upper peaks 51 of the upper teeth 46 in the first and second jaw portions 42a, 42b form an angle δ relative to the longitudinal axis 18. Referring back to FIG. 12a, in some configurations, in the gripping position 32, one nor more gaps 94 may be formed between corresponding surfaces of the upper teeth 46, lower teeth 62, and/or sockets 60.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. A forceps comprising:
   a gripping assembly comprising:
      an upper jaw including a proximal end and a distal end, the upper jaw includes an upper tooth having an upper proximally facing canted tooth surface and an upper distally facing canted tooth surface;
      a lower jaw including a proximal end and a distal end, the lower jaw includes a socket having a lower distally facing canted socket surface and a lower proximally facing socket surface;
      wherein the upper jaw, the lower jaw, or both are moveable so that the gripping assembly moves between an open position and a gripping position; and
      wherein in the gripping position, a first gap is defined between the upper distally facing canted tooth surface and the lower proximally facing socket surface and a second gap is defined as a substantially constant distance, continuously extending, between the upper proximally facing canted tooth surface and the lower distally facing canted socket surface;
      wherein an upper peak is defined between the upper proximally facing canted tooth surface and the upper distally facing canted tooth surface, and a valley is defined between the lower distally facing canted socket surface and the lower proximally facing socket surface;
      wherein an axis extending through the upper peak and generally perpendicular to a longitudinal axis of the gripping assembly is offset relative to an axis extending through the valley and generally perpendicular to the longitudinal axis of the gripping assembly; and
      wherein a first angle of the lower distally facing canted socket surface, relative to a longitudinal axis of the lower jaw extending between the proximal end of the lower jaw and the distal end of the lower jaw is similar to a second angle of the upper proximally facing canted tooth surface relative to the longitudinal axis of the gripping assembly, the longitudinal axis of the gripping assembly extending between a proximal end of the gripping assembly and a distal end of the gripping assembly;
      wherein the lower proximally facing socket surface has a third angle relative to the longitudinal axis of the lower jaw; and
      wherein the upper distally facing canted tooth surface has a fourth angle relative to the longitudinal axis of the gripping assembly different from the third angle.

2. The forceps of claim 1, wherein a width of the first gap increases from an upper portion of the lower proximally facing socket surface to the valley.

3. The forceps of claim 2, wherein the lower proximally facing socket surface is generally vertical relative to the longitudinal axis of the lower jaw extending between the proximal end of the lower jaw and the distal end of the lower jaw.

4. The forceps of claim 1, wherein the upper jaw includes a plurality of upper teeth; and
   wherein an amplitude of the upper teeth decreases from the distal end of the upper jaw to the proximal end of the upper jaw.

5. The forceps of claim 1, wherein the upper jaw and the lower jaw each include camming sections located proximally to the upper tooth and the socket respectively;
   wherein applying a force onto the camming sections moves one or both of the upper jaw and the lower jaw towards each other to move the gripping assembly to the gripping position; and
   wherein removing the force from the camming sections moves one or both of the upper jaw and the lower jaw away from one another to move the gripping assembly to the open position.

6. The forceps of claim 1, wherein one of the upper jaw and the lower jaw is connected to a source of electrosurgical energy so that in the gripping position bipolar energy can be conducted through tissue configured to be gripped between the upper jaw and the lower jaw.

7. The forceps of claim 1, wherein the upper jaw is generally U-shaped defining an upper channel located between first and second jaw portions, the upper jaw includes a plurality of upper teeth that extend from the first and second jaw portions;
   wherein the lower jaw is generally U-shaped defining a lower channel generally opposing the upper channel and located between third and fourth jaw portions, the lower jaw includes a plurality of sockets disposed along the third and fourth jaw portions; and
   wherein a cutting member is located between the upper channel and the lower channel, the cutting member is moveable relative to the upper jaw and the lower jaw when the gripping assembly is in the gripping position.

8. The forceps of claim 1, wherein in the gripping position, the upper proximally facing canted tooth surface is in contact with the lower distally facing canted socket surface.

9. A medical instrument comprising:
   a forceps including:
      a first jaw including a first tooth having:
         i. a first proximally facing canted tooth surface;
         ii. a first distally facing canted tooth surface; and
      a second jaw including a second tooth having:
         i. a second proximally facing tooth surface; and
         ii. a second distally facing canted tooth surface;
      wherein the second jaw includes a third tooth having:
         i. a third proximally facing tooth surface; and
         ii. a third distally facing tooth surface;
   wherein in a gripping position, the first distally facing canted tooth surface generally opposes the third proximally facing tooth surface so that a first gap is defined therebetween;
   wherein a width of the first gap increases from an upper portion of the third proximally facing tooth surface to a lower portion of the third proximally facing tooth surface;
   wherein the third proximally facing tooth surface is perpendicular relative to a longitudinal axis of the second jaw extending between a proximal end of the second jaw and a distal end of the second jaw;
   wherein a second gap between at least a portion of the first proximally facing canted tooth surface and a corresponding portion of the second distally facing canted tooth surface is nearly constant;
   wherein an upper peak is defined between the first proximally facing canted tooth surface and the first distally facing canted tooth surface, and a valley is defined between the second distally facing canted tooth surface and the third proximally facing tooth surface, and
   wherein an axis extending through the upper peak and generally perpendicular to the longitudinal axis of the second jaw is offset relative to an axis extending through the valley and generally perpendicular to the longitudinal axis of the second jaw.

10. The medical instrument of claim 9, wherein an angular position of the second distally facing canted tooth surface relative to the longitudinal axis of the second jaw sufficiently corresponds to an angular position of the first proximally facing canted tooth surface relative to the longitudinal axis of the second jaw.

11. The medical instrument of claim 9, wherein in the gripping position, the first proximally facing canted tooth surface is in contact with the second distally facing canted tooth surface.

12. The medical instrument of claim 9, wherein the third distally facing tooth surface is canted and forms an angle that is less than 90 degrees relative the longitudinal axis of the second jaw.

13. A jaw assembly comprising:
   an upper jaw comprising an upper tooth, the upper tooth comprising:
      an upper proximally facing tooth surface, an upper distally facing tooth surface, and an upper jaw peak that is defined between the upper proximally facing tooth surface and the upper distally facing tooth surface; and
   a lower jaw comprising a lower socket, the lower socket comprising:
      a lower distally facing socket surface, a lower proximally facing socket surface, and a lower jaw valley that is defined between the lower distally facing socket surface and the lower proximally facing socket surface;
   wherein a first gap is defined between the upper proximally facing tooth surface and the lower distally facing socket surface, and a second gap is defined between the upper distally facing tooth surface and the lower proximally facing socket surface;
   wherein a width of the first gap decreases continuously in a proximal direction from the upper jaw peak, and a width of the second gap decreases continuously in a distal direction from the upper jaw peak; and
   wherein an axis extending through the upper jaw peak and the lower jaw valley is generally perpendicular to a longitudinal axis of the jaw assembly.

14. The jaw assembly according to claim 13, wherein the upper jaw comprises a plurality of upper teeth and the lower jaw comprises a plurality of lower teeth; and
   wherein an amplitude of the upper teeth is greater than an amplitude of the lower teeth.

* * * * *